US00PP30355P2

(12) United States Plant Patent
Lee

(10) Patent No.: US PP30,355 P2
(45) Date of Patent: Apr. 9, 2019

(54) ***VIBURNUM* PLANT NAMED 'BLV01'**

(50) Latin Name: *Viburnum luzonicum*
Varietal Denomination: BLV01

(71) Applicant: Robert Edward Lee, Independence, LA (US)

(72) Inventor: Robert Edward Lee, Independence, LA (US)

(73) Assignee: Plant Development Services Inc., Loxley, AL (US)

( * ) Notice: Subject to any disclaimer, the term of this patent is extended or adjusted under 35 U.S.C. 154(b) by 0 days.

(21) Appl. No.: 15/732,125

(22) Filed: Sep. 19, 2017

(51) Int. Cl.
*A01H 5/02* (2018.01)

(52) U.S. Cl.
USPC ..... Plt./226

(58) Field of Classification Search
USPC ..... Plt./226

CPC ... A01H 5/02; A01H 5/12; A01H 5/00; A01H 5/08; A01H 6/00
See application file for complete search history.

(56) References Cited

PUBLICATIONS

Issuu Flowerwood Catalog 2016-2017, retrieved on Aug. 16, 2018, retrieved from the Internet at https://issuu.com/kschmucker/docs/fw-catalog-2016-2017, cover page, pp. 21 and 75-76. (Year: 2017).*
Southern Living Plants Snow Joey *Viburnum*, retrieved on Aug. 16, 2018, retrieved from the Internet at http://southernlivingplants.com/shrubs/plant/snow-joey-viburnum, 4 pp. (Year: 2018).*

* cited by examiner

*Primary Examiner* — June Hwu
(74) *Attorney, Agent, or Firm* — Cassandra Bright

(57) ABSTRACT

A new and distinct *Viburnum* cultivar named 'BLV01' is disclosed, characterized by profuse white blooms in the Spring and heavy fruit set of red drupes in the Fall, persisting through the Winter. Plants have a moderate, controlled growth habit and tolerate environment stressors well. The new variety is a *Viburnum*, normally produced as an outdoor garden or container plant.

2 Drawing Sheets

Latin name of the genus and species: *Viburnum luzonicum.*

Variety denomination: 'BLV01'.

BACKGROUND OF THE INVENTION

The new *Viburnum* cultivar is a product of a planned breeding program. The inventor grew several unnamed, unpatented *Viburnum luzonicum* plants and collected seed from the resulting open-pollination. The parent varieties are unidentified. Seed was collected and sown in the Fall of 2002 at a commercial nursery in Independence, La. The inventor planted bulk collected open-pollinated seed, growing seedlings out to the flowering stage.

This interesting seedling was first selected during 2007 in a commercial nursery in Independence, La. The inventor observed this interesting plant over several years, noting the consistently abundant flowering.

Asexual reproduction of the new cultivar 'BLV01' by softwood cuttings was first performed during the summer of 2010, at a commercial greenhouse in Independence, La. Subsequent propagation has shown that the unique features of this cultivar are stable and reproduced true to type in two successive generations.

SUMMARY OF THE INVENTION

The cultivar 'BLV01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BLV01' These characteristics in combination distinguish 'BLV01' as a new and distinct *Viburnum* cultivar:

1. Profuse white blooms in the Spring.
2. Heavy red berry set persisting throughout the Winter.
3. Deciduous shrub with bronze purple/red Fall leaf color
4. Easy to propagate from softwood cuttings.
5. Hardy in USDA zones 7-10.
6. Performs better in well drained moist acid soil, however can adapt to different soil conditions.
6. Tolerant to environmental related stress with no insect or disease problems.
7. Tolerates full sun to partial shade conditions.
8. Well established plants have shown good drought resistance.
9. Growth rate is moderate
10 Easy to maintain to a height of 6 to 8 feet and 4 to 6 feet wide
11. Habit is broad rounded with open outer branches
12. Great for open woodland shrub, hedges, foundations, screens and borders

PARENT COMPARISON

Parent varieties are unknown.

COMMERCIAL COMPARISON

Plants of the new cultivar 'BLV01' can be compared to the unpatented, unnamed commercial *Viburnum luzonicum* sold in the trade. Plants are similar in most horticultural characteristics; however 'BLV01' differs in the following:

1. The new variety reaches a mature height of 6 to 8 feet and 4 to 6 feet wide, compared to 8 to 15 feet tall and 8 to 15 feet wide mature size typical of *Viburnum luzonicum*.
2. Plants of the new variety are less vigorous and more controlled in growth.
3. The new variety produces more flowers per plant.
4. The new variety sets fruit more heavily.

BRIEF DESCRIPTION OF THE PHOTOGRAPHS

Figure 1:
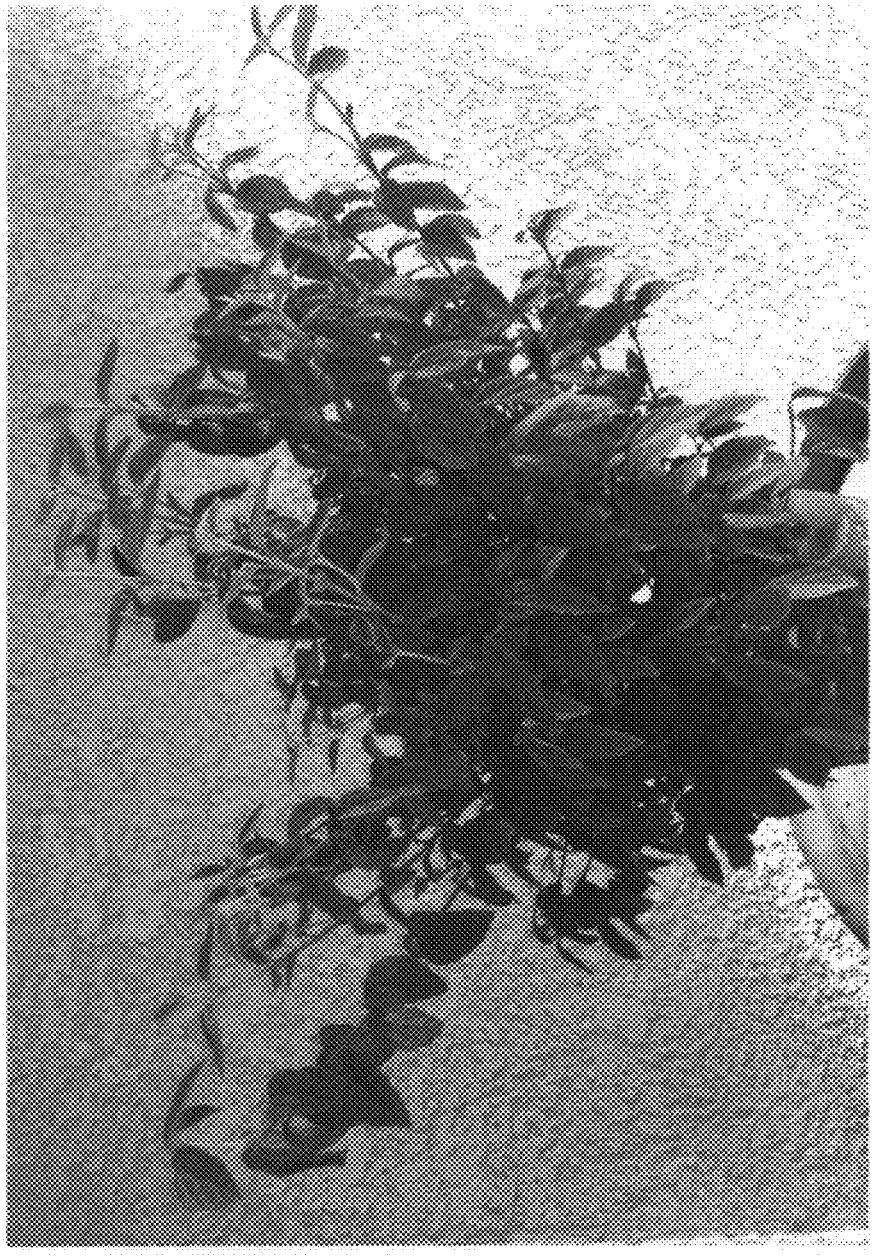

The accompanying photograph in FIG. 1 illustrates in full color a typical plant of 'BLV01' grown outdoors in a 2 gallon nursery pot, in Loxley, Ala. during Summer.

Figure 2:
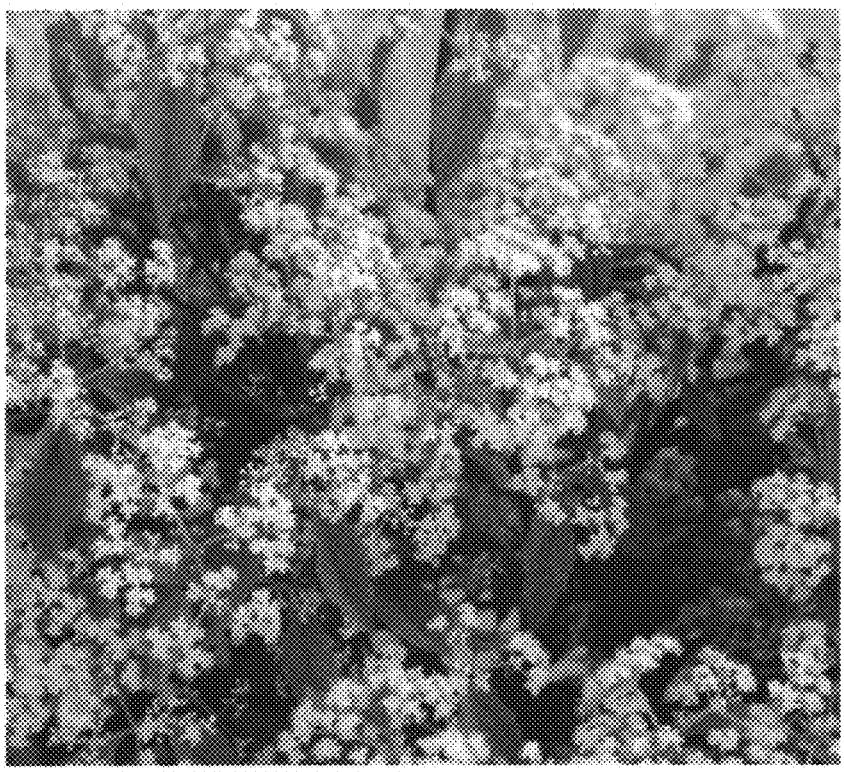

FIG. 2 illustrates in full color typical inflorescences of 'BLV01'. Age of the plant photographed is approximately 2 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BLV01' plants grown outdoors at a commercial nursery in Loxley, Ala. under natural lighting. Measurements were taken during Summer of 2017. The plants described were approximately 2 to 3 years old in 3 gallon containers. The growing temperature ranged from 5° C. to 27° C. Measurements and numerical values represent averages of typical plant types.

Botanical classification: *Viburnum luzonicum* 'BLV01'.

PROPAGATION

Time to initiate roots: About 15 to 20 days at approximately 24° C.

Root description: Dense density freely branching. Root thickness from thick to thin. White to brown in color, not effectively measured with a color chart.

Time to produce a rooted young plant: About 90 days at 24° C.

PLANT

Plant type: Deciduous perennial shrub.
Age of plant described: Approximately 2 years old.
Pot size of plant described: 3 gallon pot.
Overall plant shape: Broad globular.
Height: 54 cm.
Plant spread: 65 cm.
Growth rate: Moderate.
Plant vigor: Good.
Branching characteristics: Opposite. Pinching required.
Length of primary lateral branches: 15 to 20 cm.
Diameter of lateral branches: 5 to 6 mm.
Quantity of lateral branches: About 4 to 6 lateral branches per main branch.
Stem:
- *Stem shape*.—Round.
- *Stem strength*.—Strong.
- *Stem color*.—Newest growth near RHS Yellow-Green 147D. Mid season growth near RHS Greyed-Green 197B, moderately covered in lenticels colored near Greyed-Green 196B. Lenticels very small, linear, less than 1 mm high and 2 mm long. Oldest growth colored near Greyed-Green 197B flushed Greyed-Purple N187B.
- *Pubescence*.—Velvety pubescence on newest growth. Mid season growth smooth except for lenticels. Oldest growth does not develop bark.
- *Aspect*.—Straight, typically occurring at 35° angles.

Internode length: Average 4 cm.

FOLIAGE

Leaf:
- *Arrangement*.—Opposite.
- *Leaf shape*.—Ovate.
- *Average length*.—Average range 4.5 to 6.5 cm.
- *Average width*.—2.5 cm.
- *Apex*.—Acute.
- *Base*.—Rounded.
- *Margin*.—Infrequent shallow dentations, some with shape serration.
- *Texture of top surface*.—Glabrous.
- *Texture of bottom surface*.—Glabrous.
- *Appearance of top surface*.—Mature foliage matte, new foliage glossy.
- *Appearance of bottom surface*.—Matte.
- *Color*.—Young foliage upper side: Near RHS Green 137C. Young foliage under side: Green 139C. Mature foliage upper side: Near RHS Green 137A Mature foliage under side: Near RHS Yellow-Green 146B. Fall foliage upper side: Near RHS Greyed-Red 179A. Some foliage flushed Greyed-Purple N186C. Fall foliage under side: Near RHS Red 42D.
- *Venation*.—Pattern: Pinnate. Color upper side: Near RHS Green 137A. Color under side: Near RHS Green 139C. Fall Color upper side: Near RHS Greyed-Orange 166C. Fall Color under side: Near RHS Greyed-Orange 166D.
- *Petiole*.—Average Length: 7 mm. Diameter: 2 mm. Petiole color upper side: Near RHS Yellow-Green 146A. Petiole color upper side: Near RHS Yellow-Green 148A. Petiole Texture upper side: Rough, extremely short, dense pubescence. Petiole Texture lower side: Rough, extremely short, dense pubescence.

FLOWER

Natural flowering season: Spring.
Inflorescence type and habit: Compound umbel.
Flower longevity on plant: About 3 weeks.
Quantity of flowers per inflorescence: Approximately 200 to 300.
Inflorescence per branch: 2 to 6.
Inflorescence size:
- *Width*.—Approximately 6-9 cm.
- *Height*.—Approximately 7 to 4-5 cm.

Individual flowers:
- *Flower form*.—Rotate, single whorl.
- *Flower aspect*.—Upward facing.

*Size*.—Diameter: Approximately 3 to 5 mm. Depth: Approximately 2 to 3 mm. Flower tube diameter: 1 mm. Flower tube length: 2 mm.

Flower other characteristics:

*Persistence*.—Self cleaning.

*Fragrance*.—Moderate to slight, sweet-musky.

Petal:

*Petal arrangement*.—Single non-overlapping whorl.

*Number of petals per flower*.—5.

*Petal shape*.—Orbicular to ovate.

*Petal base*.—Obtuse.

*Margin*.—Entire.

*Tip shape*.—Obtuse.

*Length*.—2 to 3 mm.

*Width*.—1 to 2 mm.

*Texture*.—Upper: Smooth, silky. Lower: Smooth, silky. Tube: Smooth.

Petal color:

*When opening*.—Upper surface: Near RHS Orange-White 159D. Lower surface: Near RHS Orange-White 159D.

*Fully opened*.—Upper surface: Near RHS White 155C. Lower surface: Near RHS White 155C. Veins upper and lower: Near RHS White 155C.

Bud:

*Shape*.—Obovate.

*Length*.—Approximately 3 mm.

*Diameter*.—Approximately 2 mm.

*Color*.—Near RHS Yellow-White 158D.

Sepals:

*Arrangement*.—Rotate, fused at base.

*Quantity*.—5.

*Shape*.—Individual sepals deltate.

*Base*.—Fused.

*Margin*.—Entire.

*Tip shape*.—Acute.

*Length*.—Less than 1 mm.

*Width*.—Less than 1 mm.

*Texture*.—Inner: Glabrous. Outer: Lightly pubescent.

*Color*.—Inner: Green 137D. Outer: Green 138A.

Peduncle:

*Length*.—Average range 2 to 4 cm.

*Diameter*.—2 to 3 mm.

*Color*.—Near RHS Yellow-Green 152C.

*Orientation*.—Approximately 15 to 85° from branch.

*Strength*.—Good.

*Texture*.—Slightly rough.

Pedicel:

*Length*.—3 to 4 mm.

*Diameter*.—1 mm.

*Color*.—Near RHS Yellow-Green 144C.

*Strength*.—Good.

*Texture*.—Glabrous.

REPRODUCTIVE ORGANS

Stamens:

*Number*.—5.

*Filament length*.—2 mm.

*Filament color*.—Near RHS Yellow-White 158D.

Anthers:

*Shape*.—Club-like, misshapen.

*Length*.—1 mm.

*Color*.—Near RHS Yellow-White 158A.

*Pollen*.—Pollen production not observed.

Pistil:

*Number*.—1.

*Length*.—3 mm.

*Style*.—Length: 2 mm. Color: Near RHS Green 143C.

*Stigma*.—Color: Near RHS Green 143C.

OTHER CHARACTERISTICS

Seeds and fruits: Small globular fruit, 1 to 3 mm in diameter. Colored near Green 144C when immature. Mature drupe colored near Red 45C during early October in Southern California. Seeds dust-like.

Disease/pest resistance: Neither resistance nor susceptibility to normal diseases and pests of *Viburnum* have been observed.

Temperature tolerance: The new variety grows in USDA zones 7 through 10.

Drought tolerance: Observed drought tolerance once established.

What is claimed is:

1. A new and distinct cultivar of *Viburnum* plant named 'BLV01' as herein illustrated and described.

* * * * *